United States Patent [19]

Fercher

[11] Patent Number: 5,847,827
[45] Date of Patent: Dec. 8, 1998

[54] COHERENCE BIOMETRY AND COHERENCE TOMOGRAPHY WITH DYNAMIC COHERENT

[75] Inventor: Adolf Friedrich Fercher, Vienna, Austria

[73] Assignee: Carl Zeiss Jena GmbH, Jena, Germany

[21] Appl. No.: 667,468

[22] Filed: Jun. 21, 1996

[30] Foreign Application Priority Data

Jun. 23, 1995 [AT] Austria ................................. 1074/95

[51] Int. Cl.$^6$ .............................. G01B 9/02; G01B 11/02
[52] U.S. Cl. ............................................ 356/345; 356/358
[58] Field of Search .................... 356/345, 357, 356/358

[56] References Cited

U.S. PATENT DOCUMENTS

| | | | |
|---|---|---|---|
| 5,321,501 | 6/1994 | Swanson et al. | 356/345 |
| 5,459,570 | 10/1995 | Swanson et al. | 356/345 |
| 5,465,147 | 11/1995 | Swanson | 356/345 |
| 5,579,112 | 11/1996 | Sugiyama et al. | 356/345 |

*Primary Examiner*—Frank G. Font
*Assistant Examiner*—Jason D. Vierra-Eisenberg
*Attorney, Agent, or Firm*—McAulay Nissen Goldberg Kiel & Hand, LLP

[57] ABSTRACT

In the application of coherence distance measurement in medical biometry and in medical coherence tomography, an interferometric measurement light path is directed on the object to be measured and is focussed in order to improve the transverse resolution. Since the focus of the measurement light beam is fixed in the axial direction, high transverse resolution cannot be achieved over the entire object depth at all interferometric measurement points along the measurement light beam. This problem is not solved merely by displacing the focus along the measurement beam, since the focus will then lose coherence with respect to the reference light and the actual interferometric measurement location will then lie outside of this focus. In accordance with the invention, a simultaneous displacement of the reference light mirror be effected synchronously with the displacement of the focus by virtue of the optics generating the focus in order to maintain the coherence of the focus. The invention provides a method in which the focus is displaced and the coherence of the focus is maintained by one and the same moving optical element.

18 Claims, 8 Drawing Sheets

COHERENCE BIOMETRY AND COHERENCE TOMOGRAPHY WITH DYNAMIC COHERENT

BACKGROUND OF THE INVENTION a) Field of the Invention

This invention relates to the field of optical medical imaging and length measurement technique.

b) Description of the Related Art

In optical coherence distance measurement [Hitzenberger, C. K.: "Optical Measurement of the Axial Eye Length by Laser Doppler Interferometry" in *Invest. Ophthalmol. Vis. Sci.* 32 (1991), No. 3, 616–624] and in optical coherence tomography [Huang, D.; Swanson, E. A.; Lin, C. P.; Schuman, J. S.; Stinson, W. G.; Chang, W.; Hee, M. R.; Flotte, T.; Gregory, K.; Puliafito, C. A.; Fujimoto, J. G.: "Optical coherence tomography", *Science* 254 (1991), 1178–1181], interferometry with light of short coherence length is used to localize the position of light-reflecting locations in the interior of objects to be measured or of objects to be imaged.

Both methods referred to above are based on interferometric measurement methods which can also be described more precisely as short-coherence interferometry. In the present case, short-coherence interferometry essentially means that light of short coherence length is used and the length to be measured in the measurement beam is determined by altering the length in the reference beam until interference patterns occur, which can only take place when there is equality between the lengths of the two beam paths within the coherence length of the light that is used. The known length of the reference beam is then equal to the length to be determined in the measurement beam. In such short-coherence interferometry, the object to be measured is either located in the measurement arm of a two-beam interferometer and the object lengths are determined by adapting the optical length of the reference arm of the interferometer to the distances in the measurement arm [Swanson, E. A.; Huang, D.; Hee, M. R.; Fujimoto, J. G.; Lin, C. P.; Puliafito, C. A.; "High-speed optical coherence domain reflectometry", *Opt. Lett.* 17 (1992), 151–153] or the object to be measured is illuminated by a dual beam ["dual beam", see Fercher, A. F.; Li, H. C.; Hitzenberger, C. K.: "Slit Lamp Laser Doppler Interferometer", *Lasers Surg. Med.* 13 (1993), 447–452] which exits from a two-beam interferometer and the object lengths are determined by adapting the path differences in said two-beam interferometer to the optical distances in the object to be measured.

In these methods a very high optical resolution (=shortest distance between two points which can still be distinguished separately) of roughly the magnitude of the coherence length $l_c = \lambda^2/\Delta\lambda$ ($\lambda$=wavelength, $\Delta l$=bandwidth of the light used), i.e., of the magnitude of several $\mu$m, is achieved in the longitudinal direction, that is, in the direction of the illuminating light beam by means of short-coherence interferometry. On the other hand, a similarly good optical resolution is achieved transversely to the illumination direction only in exceptional cases. In particular, the transverse optical resolution is not equally good over the entire object depth. A high and uniformly favorable resolution over the entire object depth is now achieved according to the present invention through the use of a so-called dynamic coherent focus. In the present case, dynamic coherent focus means the focus of a light bundle which always remains coherent with respect to the reference light even when displaced in space. This method according to the invention is explained more fully hereinafter with reference to the drawings.

Focussed light bundles have long been used for precise length determination and object positioning. However, this has always involved determination of the position of object surfaces and not the determination of the depth structure of the objects. For example, the German Offenlegungsschrift DE 2 333 281 (laid open date: 1/17/1974) describes a method for adjusting the focal point of an optical system on the basis of interferometry (but not short-coherence interferometry). For this purpose, the measurement beam is focussed on the object surface and the reflected light is interfered with a reference light beam. The shape of the interference fringes then forms a criterion for establishing whether or not the object surface is in focus. Therefore, this method is only suitable for determining the position of individual object surfaces and does not represent a direct alternative to the method according to the invention. Further, statistical interference patterns, so-called speckle, which substantially defy interpretation occur in the presence of depth structure. Another method for determining the position of object surfaces is described in U.S. Pat. No. 4,589,773 (patent date: 5/20/1986). In this case, the object surface is obliquely illuminated by a measurement light bundle as is carried out in the known optical light-section microscope. A longitudinal displacement of the object accordingly results in a transverse displacement of the light spot on the object surface. This light spot is imaged on a special photodetector which converts the offset of the light spot from the reference position into an electrical signal and can thus determine the position of the object. This method is also only suitable for determining the position of individual surfaces, but not for recording the depth structure of an object. It does not work by interferometry and hence has no interferometric sensitivity and can therefore not be compared with the method according to the invention.

Other methods for determining the position of individual object surfaces are known in the context of focussing problems in CD's, e.g., U.S. Pat. No. 4,631,395 (patent date: 12/23/1986) and U.S. Pat. No. 4,866,262 (patent date: 9/12/1989). These methods are also only suited to determine the position of individual surfaces but not for recording the depth structure of an object. They do not work by interferometry and are therefore not comparable with the method according to the invention.

On the other hand, the problem in relation to coherence biometry and coherence tomography is addressed in the international PCT Application WO 92/19930 "Method and apparatus for optical imaging and measurement" (priority date: Apr. 29, 1991; Inventors: Huang, D.; Fujimoto, J. G.; Puliafito, C. A.; Lin, C. P.; Schuman, J. S.). In this reference the present problem of achieving a high, uniformly good resolution over the entire object depth is met in that the deflecting mirror is moved in the reference beam path synchronously with the movement of the measurement focus. This method is explained more fully hereinafter with reference to FIG. 5. While a synchronous movement of the measurement focus and deflecting mirror in the reference beam is manageable in terms of technique, it represents considerable additional expenditure on mechanical and electronic equipment. Further, the geometric displacement of the measurement focus will generally not correspond to the change in optical length in the reference beam since there are different refractive indices in the measurement beam path and in the reference beam path. The present invention solves both problems by means of the coherent dynamic focus in which the displacement of focus and the balancing of the optical lengths of the measurement beam and reference beam are effected by means of the displacement of an individual optical element.

BRIEF DESCRIPTION OF THE DRAWINGS

In the drawings.

The method according to the invention is explained with reference to the following figures.

Figure 1:
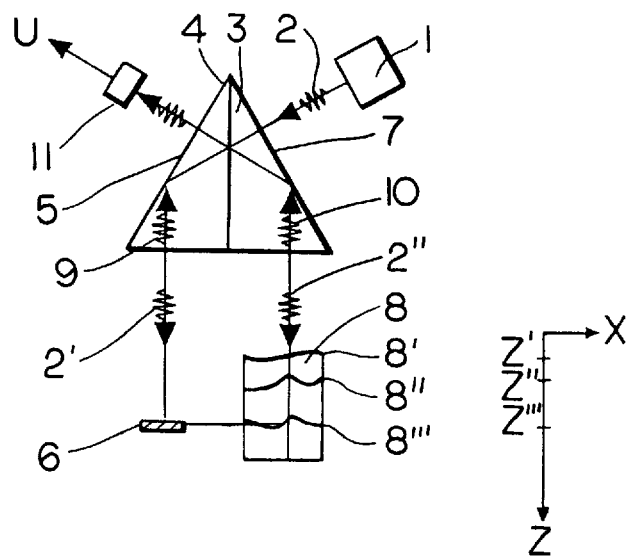
FIG. 1 shows optical coherence distance measurement based on an interferometer with a Kösters double prism (also called "Kösters interferometer" hereinafter for the sake of brevity)

The following reference numbers are used:
1 light source
2 light beam of short coherence length
2' reference beam of short coherence length
2" light beam of short coherence length in the measurement arm of the interferometer; measurement light beam illuminating the object
3 Kösters double-prism interferometer
4 beam splitter surface
5 outer surface of the Kösters prism
6 end mirror of the reference beam path
7 outer surface of the Kösters prism
8 object to be measured
8', 8" and 8'" light-reflecting structures of the object to be measured
9 reference light beam
10 measurement beam reflected by the object
11 photodetector
12 optics focussing the measurement light on the object to be measured
13 measurement focus
14 deflecting mirror, rotating or oscillating scanning mirror
15, 15', 15" different directions of the measurement beam 10
16 tomographic imaging
17 rigid connection between reference mirror 6 and focussing optics 12
20 beam splitter
21 lens optics
22 focus, center of curvature of concave mirror 24
23 beam splitter
24, 24', 24" measurement light mirror (concave mirror)
25 focus, center of curvature of concave mirror 24
25' image of focus 25
26 beam splitter
27, 27' lens optics
28 object to be measured (eye)
28' cornea
28" eye lens
30 fundus oculi
32 beam focus
33 pinhole diaphragm
34 roof prism
35 beam splitter
36 photodetector
37 lens optics
38 collective lens
39 plane mirror
40 convex mirror
41 optics
42 virtual beam focus, center of curvature of convex mirror and focus of optics 41
43 optics
44 dispersive lens
45 plane mirror
46 common focus of optics 41 and dispersive lens 44
50 optics
51 beam focus, center of curvature of concave mirror 55
52 beam splitter
53 focus of reference light bundle 2'
54 concave reference mirror
55 measurement light mirror (concave mirror)
56' beam focus, center of curvature of concave mirror 55
57 beam splitter
58 optics
59 front surface of the cornea
60 pinhole diaphragm
61 optics
62 photodetector
63 beam focus
70 deflecting mirror
71 beam splitter
72 beam focus
73 lens optics
74 lens optics
75 tomographic scanning mirror
76 focus
77 focus
78 optics
79 pinhole diaphragm
80 resilient clip
81 stable base 82 plunger core
83 magnet coil
84 power source
85 rotating disk
86 disk axis
90 photodetector
91 roof prism
92 deflecting mirror
93 optics
94 optics
95 beam splitter
99 fiber-optics interferometer
100 focussing optics
101 input of fiber-optics interferometer
102 optics
103 reference mirror
104 optics
105 beam splitter
106 moving measurement light mirror
107 moving focus
108 optics
109 tomographic scanning mirror
110 focus
111 optics
112 output of fiber-optics interferometer
113 optics
114 photodetector
115 fiber-optics coupler

DETAILED DESCRIPTION OF THE INVENTION

An interferometer with a Kösters double prism is shown in FIG. 1 and, in view of the simplicity of its beam path, is used to explain the complex problems upon which the present Patent Application is based.

In the beam path shown in FIG. 1, a light source 1 emits a light beam 2 of short coherence length (indicated by short wave trains), but with perfect spatial coherence. Such light sources include, e.g., multimode semiconductor lasers, superluminescent diodes, or tunable semiconductor lasers. The light beam 2 strikes an interferometer with a Kösters double prism 3 having a beam splitter surface 4. The Kösters double prism comprises two right-angle prisms which are cemented together by their longer sides. The component 2' of the light beam 2 penetrating the beam splitter surface 4 strikes the outer surface 5 of the Kösters double prism as a reference beam and is reflected to the reference mirror 6 of the interferometer. The component of the light beam 2 reflected at the beam splitter surface 4 is directed as a measurement beam 2" to the measurement object 8 with the light-reflecting structures 8', 8", and 8''' by the outer surface 7 of the Kösters double prism.

The light beam striking the reference mirror 6 is reflected by the latter and strikes the beam splitter surface 4 via the outer surface 5 of the Kösters interferometer as a reference beam 9 and is reflected from the beam splitter surface 4 onto the photodetector 11 at the interferometer output. Similarly, the measurement beams 10 reflected by the object structures 8', 8", 8''' are likewise directed via the outer surface 7, through the beam splitter surface 4 onto the photodetector 11 at the interferometer output and interfere with the reference beam 9.

Before proceeding with the description of the invention, reference is had to a fundamental principle of all interferometers. In interferometric beam paths, the light emitted by a light source is first divided by beam splitting, e.g., by means of a semitransparent mirror (beam splitter surface 4 in FIG. 1), into a reference beam (2' in FIG. 1) and a measurement beam (2" in FIG. 1). After proceeding along different paths, the measurement beam (10) returning from the measurement object and the reference beam (9) returning from the reference mirror are combined, e.g., by means of a semitransparent mirror (again, beam splitter surface 4 in FIG. 1), and the two beams interfere. Differences in the optical length of the two partial beams can then be determined from the interference state.

The short-coherence interferometry used in the present case works in a different way: The position of the reference mirror 6 in FIG. 1 positively defines the length of the reference beam path (from 4 to 6 and back to 4 again in FIG. 1). Short-coherence interferometry makes use of light of short coherence length. However, interference occurs only when the interference condition is met, i.e., when the optical length (=geometric length times index of refraction along the path) of the reference beam path within a tolerance corresponding to the magnitude of the coherence length $l_C$ of the light that is used is equal to the optical length of the measurement beam path (from 4 to the actual interferometric measurement position 8''' and back to 4 in FIG. 1). Thus, the length of the reference beam path defines the location in the object to be measured by interferometry, i.e., the actual interferometric measurement position. The actual interferometric measurement position is that position in the measurement beam path for which the optical length in the measurement beam path from the splitting of the beam to the combination of the beams is equal to the optical length of the reference beam path from the splitting of the beam to the combination of the beams. Accordingly, the length to be measured in the measurement beam path is obtained from the easily measurable length of the reference beam path. This is explained in still more detail with reference to the interferometer shown in FIG. 1.

In order to detect the entire depth of the object 8 to be measured in the z-direction, the reference mirror 6 must be displaced by a suitable distance in the direction of the reference beam 2'. The interference occurring at the interferometer output is, on the one hand, a criterion for the position of the actual measurement position or the position of the light-reflecting location in the object (located at the same distance from the splitter surface 4 as the reference mirror) and, on the other hand, is also representative of the intensity of the light reflectance from the respective actual measurement position. That is, the position of the reference mirror gives the z-position of this actual measurement position in the interior of the object and the intensity of the measurement signal U is a measurement of the intensity of the light reflectance in the measurement location. Thus, briefly stated, the measuring method of short-coherence interferometry consists in determining the position of the respective light-reflecting locations in the interior of the object—e.g., location 8''' in FIG. 1—from the position of the reference mirror—e.g., the position of 6 in FIG. 1.

Figure 2:
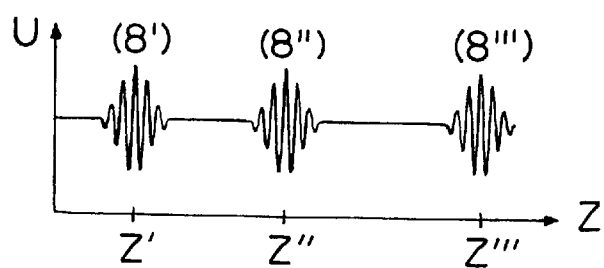
FIG. 2 shows a photodetector signal U along the z-position of the reference mirror in optical coherence distance measurement corresponding to the A-image in medical ultrasound technique.

The reference mirror 6 is displaced, e.g., by means of a table controlled by a stepper motor or by electrodynamic means or—with shorter measurement paths piezoelectrical means. It can also execute an oscillating movement or another type of movement. Whenever the length of the reference light beam is equal to the length of the measurement light beam to a light-reflecting location in the object, interference is observed at the interferometer output and the photodetector 11 delivers an electrical a.c. signal U. When the positions z of the reference mirror 6 are recorded and the photodetector 11 delivers an a.c. signal, e.g., with reference to the positions of the table controlled by a stepper motor and the associated photodetector signals U, the z-positions of the respective light-reflecting locations along the measurement beam 10 in the object are obtained as is indicated in FIG. 2. Such measurement will be referred to hereinafter as "A-scan". or "linear scanning". The results correspond to the "A-image" known from medical ultrasound technique. This is the fundamental principle behind coherence distance measurement.

In coherence tomography, a plurality of such interferometric distance measurements is carried out at adjacent (e.g., in the x-direction) locations and combined to form an image. When the light beam 2" (see FIG. 1) illuminating the object is displaced after every A-scan relative to the object, e.g., in the x-direction, the object structure in the z-direction is obtained line-by-line with every other x-position and these lines can be combined to form a section image (tomogram). The intensity of the occurring interference pattern is a measurement for the intensity of the light reflectance in the measurement location. In this way, an image corresponding to the "B-image" in medical ultrasound technique is obtained. This is the fundamental principle behind optical coherence tomography.

Figure 3:
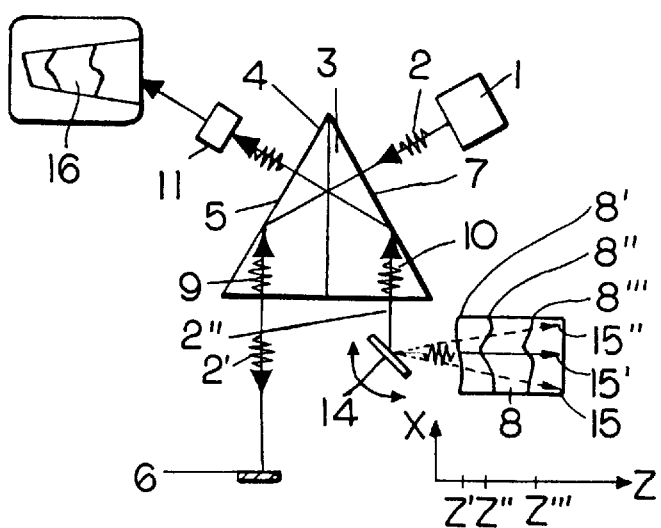
FIG. 3 shows an example of an interferometer for coherence tomography.

A displacement of the light beam 2" illuminating the object can also be effected, for instance, by means of a rotating or oscillating deflecting mirror 14 as is shown in FIG. 3. Depending on the orientation of the deflecting mirror 14, the measurement is carried out at the object 8 in different directions 15, 15' and 15" and at corresponding x-positions. The different intensity of the photodetector signals occurring at the interferometer output can be used—e.g., after electronic bandpass filtering—for linewise construction of a tomographic image 16.

Figure 4:
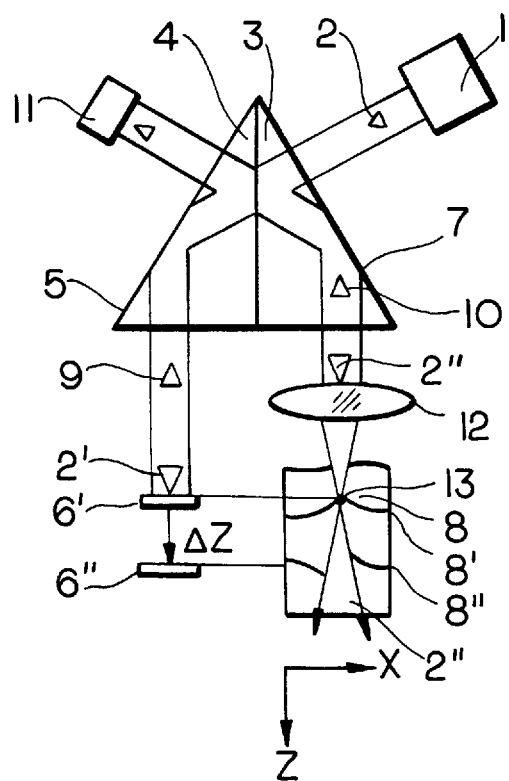
FIG. 4 shows optical coherence distance measurement based on an interferometer with a Kösters double prism with focussing of the object light beam.

As was mentioned above, the optical resolution in the longitudinal direction (=z-direction) of the interferometric measurement path is roughly of the order of magnitude of the coherence length $l_C$ of the light bundle 2. In modern superluminescent diodes, the value $l_C$ can be very small, e.g., 10 μm. The longitudinal resolution is correspondingly favorable in coherence distance measurement and coherence tomography. However, in this case the width of the light bundle is averaged in the (transverse) plane orthogonal to the z-direction (see FIG. 4). No details can be distinguished within the width of the measurement beam 2". In order to overcome this problem, the measurement beam 2" directed on the measurement object can be focussed by means of lens optics 12 as is indicated in FIG. 4. Evidently, maximum transverse resolution is now obtained in the measurement focus 13. However, this resolution diminishes as the distance from the measurement focus increases in the z-direction. Optimum transverse resolution is obtained only where the actual interferometric measurement position lies in the measurement focus (13), i.e., only where the optical length of the reference beam path is equal to the optical length of the measurement beam path from the splitting of the beam to the measurement focus 13 and continuing to the combination of the beams. Outside of this location, the transverse resolution along the interferometric measurement path is considerably worse.

Figure 5:
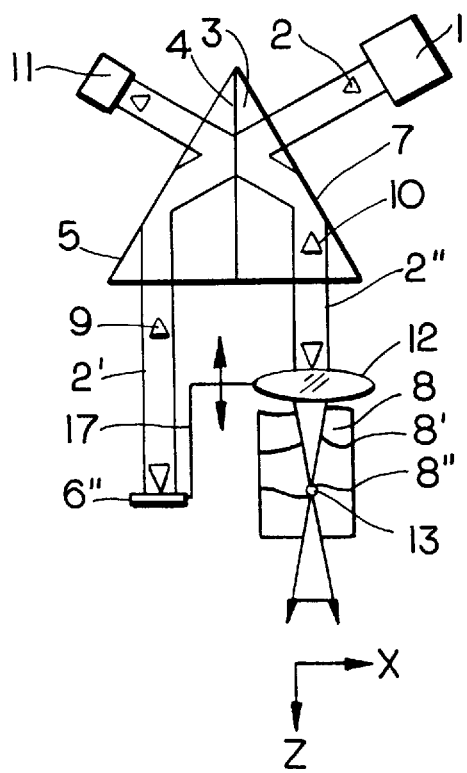
FIG. 5 shows optical coherence distance measurement based on an interferometer with a Kösters double prism in which the reference mirror is displaced by a distance $\Delta z$ in relation to FIG. 4 and the focussing optics are displaced by the same distance $\Delta z$.

This problem is solved in the PCT Application WO 92/19930 "Method and apparatus for optical imaging and measurement", mentioned above, in that the deflecting mirror is moved in the reference beam path synchronously with the movement of the measurement focus. This method is indicated in FIG. 5 by a rigid connection 17 ensuring a synchronous movement in the z-direction (represented by the double arrow) of the reference mirror 6 and focussing optics 12. This corresponds to the method described in WO 92/19930.

Although a synchronous movement of the measurement focus and deflecting mirror in the reference beam can be achieved in terms of technique, it represents a considerable additional expenditure on mechanical devices and electronics on the one hand. On the other hand, the geometric displacement of the measurement focus will generally not correspond to the change in optical length in the reference beam, since there are different refractive indices in the measurement beam path and in the reference beam path. This method corresponds to the current state of the art. The present invention solves both problems by means of the coherent dynamic focus in which the displacement of the focus and the equilibrium of the optical lengths of the measurement beam and reference beam are effected by displacing an individual optical element.

Therefore, the technical objective addressed by the present invention consists on the one hand in realizing a focus which is moved along the interferometric measurement path and on the other hand in maintaining, at the same time, the equality between the optical lengths of the reference beam path and measurement beam path until this focus by means of an individual moving optical element.

The invention achieves a uniformly good, high optical transverse resolution along the entire interferometric measurement path in that the equilibrium of the optical lengths of the reference beam path and measurement beam path to the (consequently coherent) measurement focus is ensured by means of suitable optical imaging of the (dynamic) focus in the object, this focus being produced by the moving optical element. The coherence of the measurement focus with respect to the reference light is achieved for all interferometric arrangements in question in that the optical length of the object light beam path for the position of the measurement focus is made equal to the optical length of the reference light beam path and this is ensured for all displacements and positions of the measurement focus (interference condition). Then only the light returning from the measurement focus is capable of interference with the reference light and only this light is used for interferometric measurement. This can be referred to as a "coherent measurement focus". As will be shown with reference to the following embodiment examples, special imaging scales must be adhered to in order to realize this principle.

The following embodiment examples show how this can be achieved in interferometer beam paths of practical importance in coherence distance measurement and coherence tomography.

Figure 6:
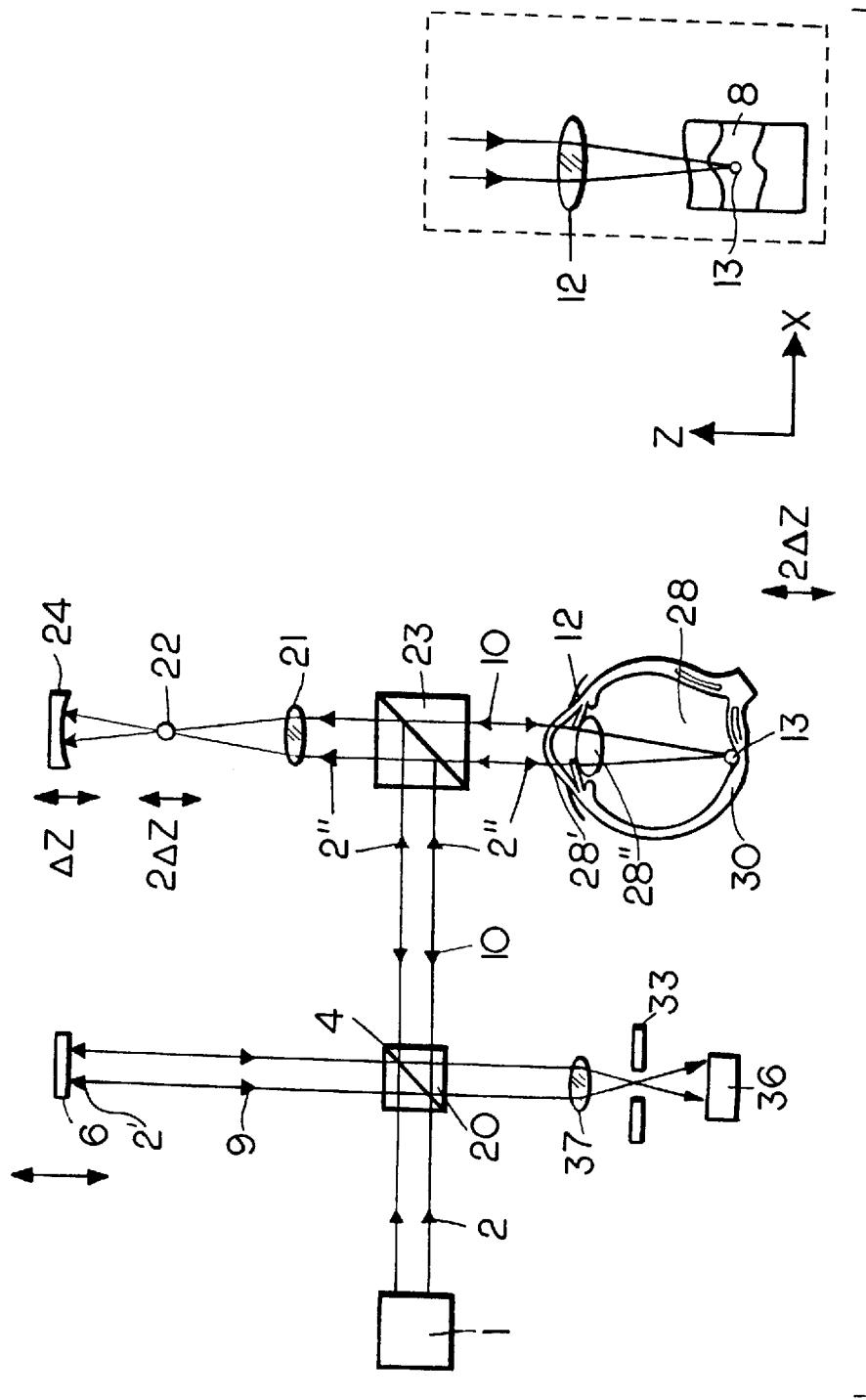
FIG. 6 shows a realization of the method according to the invention using the example of the measurement of intraocular distances by means of short-coherence interferometry based on a Michelson interferometer.

FIG. 6 shows a first example of an arrangement for coherence distance measurement in ophthalmology applying the method according to the invention. This involves, for example, the measurement of distances between light-reflecting layers in the fundus oculi 30 which in the present case represents the measurement object within the narrower meaning. In the present example, the cornea 28' and eye lens 28" perform the function of the focussing optics 12. Rather than the fundus oculi, another object 8 can also be measured. In that case, the measurement beam is focussed on this object 8 by means of optics 12 as is indicated in the boxes shown in dashed lines at the lower right-hand corner of FIG. 6.

In FIG. 6, the light source 1 emits a light beam 2 of short coherence length which strikes the beam splitter 20, where the beam is split into a reference beam 2' and a measurement beam 2" at the splitter surface 4. The component of the light beam 2 traversing the beam splitter surface 4 travels via the beam splitter 23 as a measurement beam 2" and is focussed in focus 22 by the optics 21. The focus 22 lies in the center of curvature of the concave mirror 24 functioning as deflecting optics. The measurement beam reflected at the concave mirror 24 is collimated again by optics 21 and strikes the measurement object (eye) 28. The ophthalmic optics (12) focus this light bundle in the measurement focus 13 on the fundus oculi 30. If a measurement object 8 other than the fundus oculi is used, the measurement beam 2" is focussed on this measurement object 8 by means of other optics 12 as is indicated by the boxes shown in dashed lines in FIG. 6. The measurement beam 10 reflected by the fundus oculi travels back to the concave mirror 24, is reflected again by the latter and is directed from the beam splitters 23 and 20 to the photodetector 36. The measurement beam 10 interferes at this location with the reference beam 9 reflected by the end mirror 6.

Further, light components which do not come from the coherent measurement focus 13 can be cut out by means of a pinhole diaphragm 33, thus improving the signal-to-noise ratio of the photodetector signals and the image quality in the coherence biometry and coherence tomography.

It should be mentioned that known state-of-the-art polarization optics are made use of in order to reduce reflection losses at the surfaces of the component parts and to optimize the beam splitters of the interferometers described herein. For example, a polarizing beam splitter is provided instead of beam splitter 23. In order for this beam splitter to function in a meaningful manner, a rotatable half-wave plate must be arranged between the beam splitters 20 and 23 in order to adjust the polarization direction. Further, a quarter-wave plate must be arranged between the beam splitter 23 and the optics 21. However, since this belongs to the known prior art, the exact functioning of these elements is not discussed in more detail.

Figure 7:
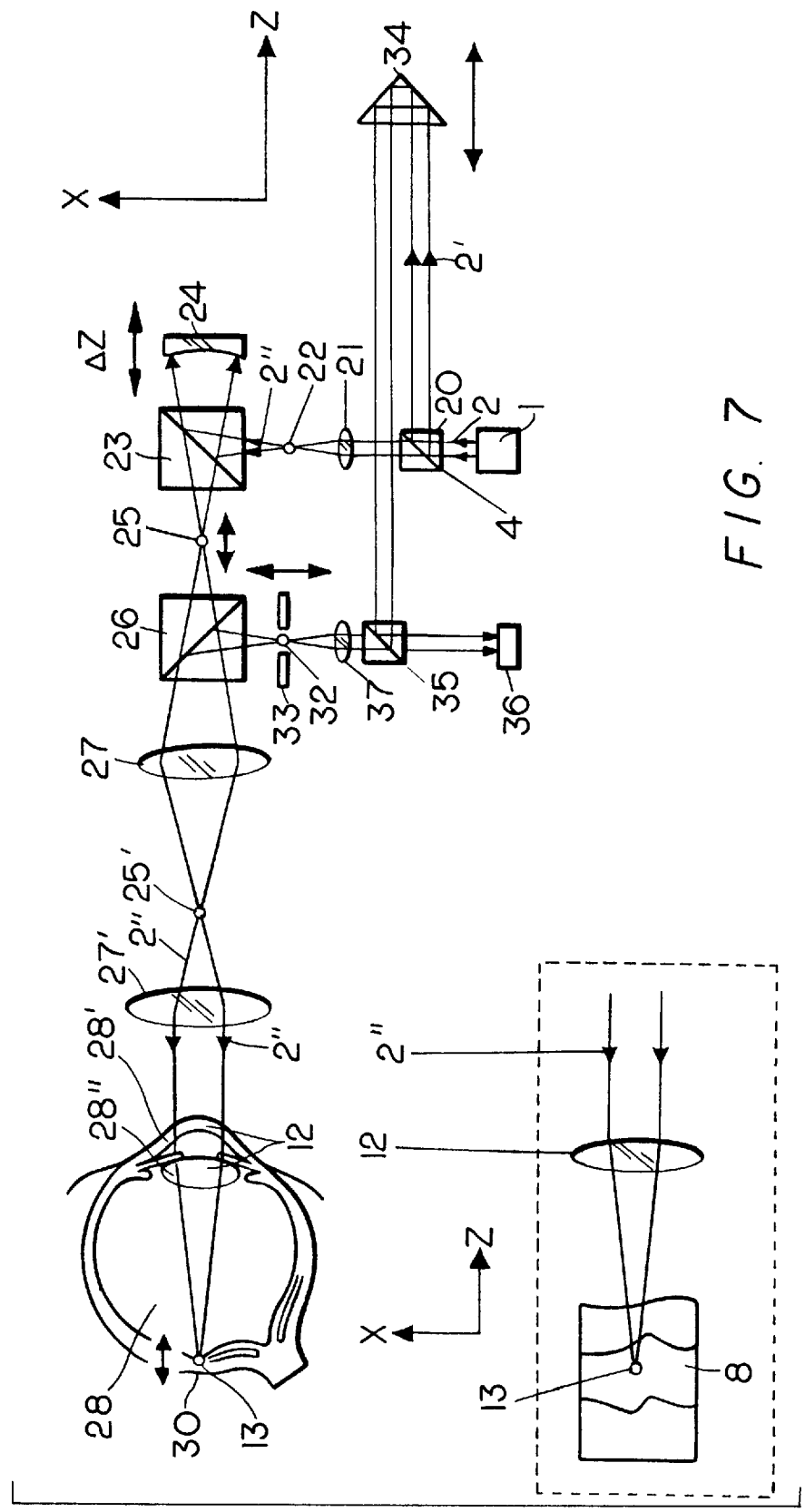
FIG. 7 shows a realization of the method according to the invention using the example of the measurement of intraocular distances by means of short-coherence interferometry based on a Mach-Zehnder beam path.

Another example of an arrangement for coherence distance measurement in ophthalmology according to the inventive method based on a beam path similar to the Mach-Zehnder interferometer is indicated in FIG. 7. In this case, also, distances are measured between light-reflecting layers in the fundus oculi 30 which in this case represents the measurement object within the narrower meaning. In this case, again, the cornea 28' and eye lens 28" perform the function of the focussing optics 12. Rather than the fundus oculi, another object 8 can also be measured. In that case, the measurement beam is focussed on this object 8 by means of optics 12 as is indicated in the boxes shown in dashed lines at the lower left-hand corner of FIG. 7.

In FIG. 7, the light source 1 emits a light beam 2 of short coherence length which strikes the beam splitter 20, where the beam is split into a reference beam 2' and a measurement beam 2". The reference beam 2' reflected at the beam splitter surface 4 is reflected by the deflecting mirror 34 to the interferometer output with the photodetector 36 and there interferes with the light bundle coming from the measurement arm of the interferometer. The deflecting mirror 34 can be displaced in the axial direction to balance the optical path lengths in the reference beam and measurement beam (calculated up to the measurement focus 13), which is indicated in the drawing by a double arrow. The component of the light beam 2 traversing the beam splitter surface 4 is focussed as a measurement beam 2" by optics 21 in a focus 22. The focus 22 lies in the center of curvature of the concave mirror 24 functioning as deflecting optics. The divergent measurement beam 2" proceeding from the focus 22 is directed by the beam splitter 23 onto the focussing measurement light mirror (concave mirror) 24 and is focussed by the latter in a focus 25 which likewise lies in the center of curvature of the concave mirror 24. The divergent measurement beam 2" traveling from the focus 25 continues on through the beam splitter 26 and is focussed in focus 25' by optics 27 and is finally directed to the measurement object (eye) 28 by optics 27'. The opthalmic optics (12) focus this light bundle in measurement focus 13 on the fundus oculi 30. If a measurement object 8 other than the fundus oculi is used, the measurement beam 2" is focussed on this measurement object 8 by means of other optics 12 as is indicated by the boxes shown in dashed lines in FIG. 7. The light returning from the measurement focus 13 then passes via the beam splitters 26 and 35 to the interferometer output and interferes with the reference light bundle.

Figure 8A:
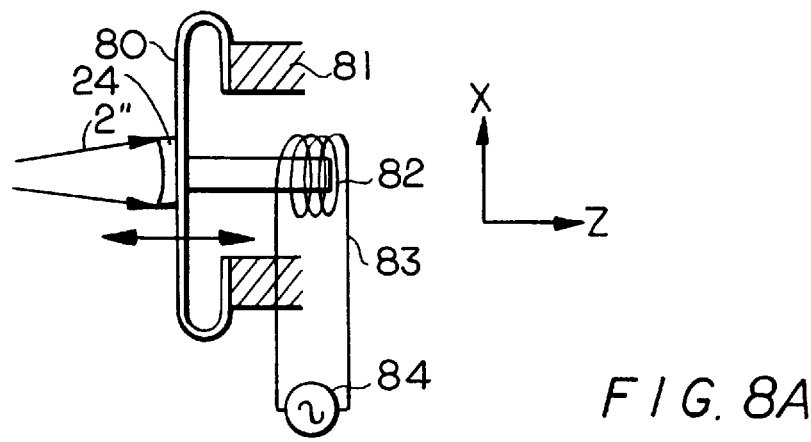
FIG. 8a shows a technical solution for producing a periodically moving focus.

In the arrangements shown in FIGS. 6 and 7, in contrast to the example shown in FIG. 5 with the Kösters interferometer, only the measurement light mirror 24 is moved in the z-direction by the distance Δz, as is indicated by the double arrow. This can be achieved, for example, by means of a scanning table which is controlled by a stepper motor or by means of a piezoelectric holder which is controlled by alternating voltage or by electrodynamic means, as is indicated in FIG. 8a. The focus 25 of the measurement beam 2" moves by distance 2.Δz in a corresponding manner. Subsequently, the coherent measurement focus 13 is also finally displaced by the object in the z-direction along the measurement path as was described above with reference to the Kösters interferometer. The position of the light-reflecting locations in the interior of the object is given positively by the respective position of the measurement light mirror 24.

FIG. 8a shows another possibility for the movement of the measurement light mirror 24. In this case, the concave mirror 24 is attached to a resilient metal clip 80. This metal clip is fastened by one end to a stable base 81. On the side located opposite to the concave mirror, a soft-magnetic plunger core 82 is fastened to the metal clip. This plunger core projects into a magnet coil 83 which delivers a suitable alternating current from a power source 84 so that the plunger core is moved in the z-direction together with the concave mirror 24 due to the effect of the magnetic field generated by the coil 83.

Figure 8B:
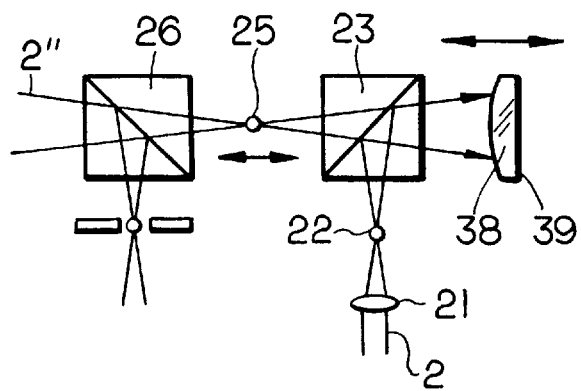
FIG. 8b shows a technical solution for producing a continuously moving focus.

Another possibility for the movement of the measurement light mirror by a distance Δz is shown in FIG. 8b. The concave mirror 24 is arranged on the circumference of a disk 85 rotating about axis 86. A plurality of measurement light mirrors 24' and 24" can also be arranged at the circumference so as to achieve relative high measurement rates at a low rotating speed of the disk 85.

Figure 9:
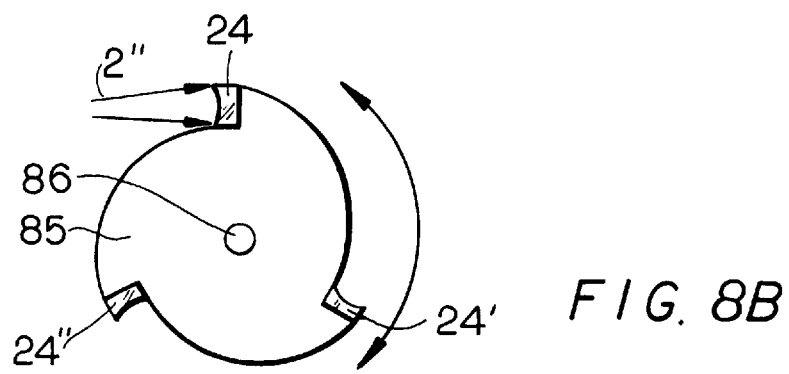
FIG. 9 shows an alternative for producing a moving focus.
Figure 10A:
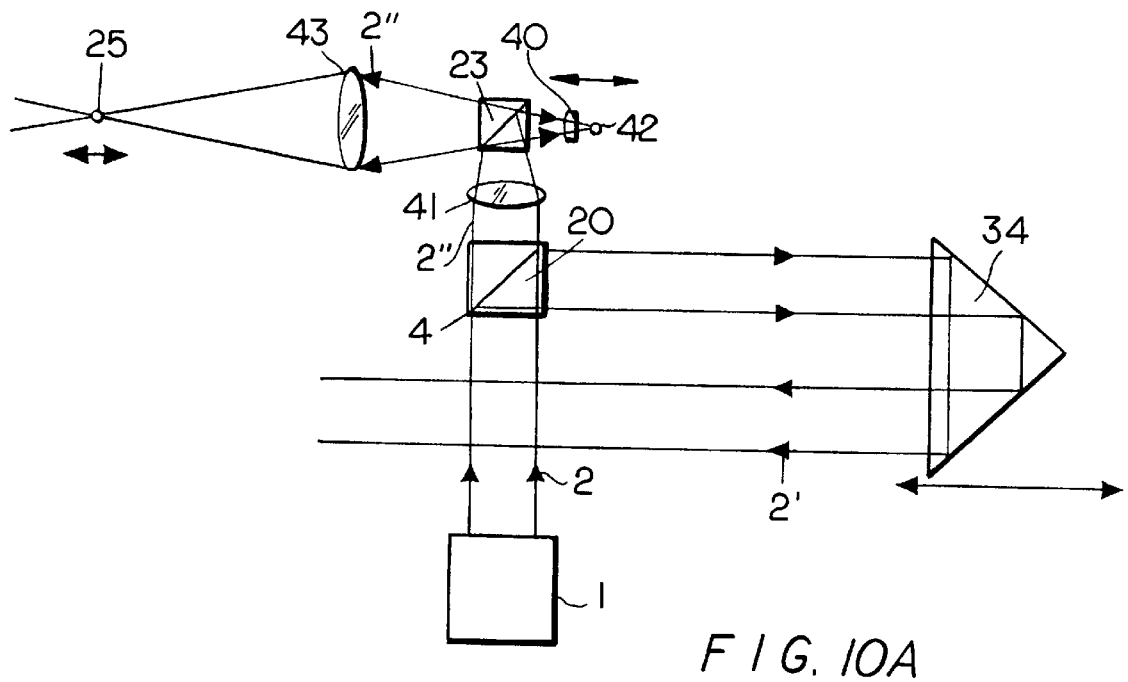
FIG. 10a shows a moving virtual focus as another alternative for producing a moving focus.
Figure 10B:
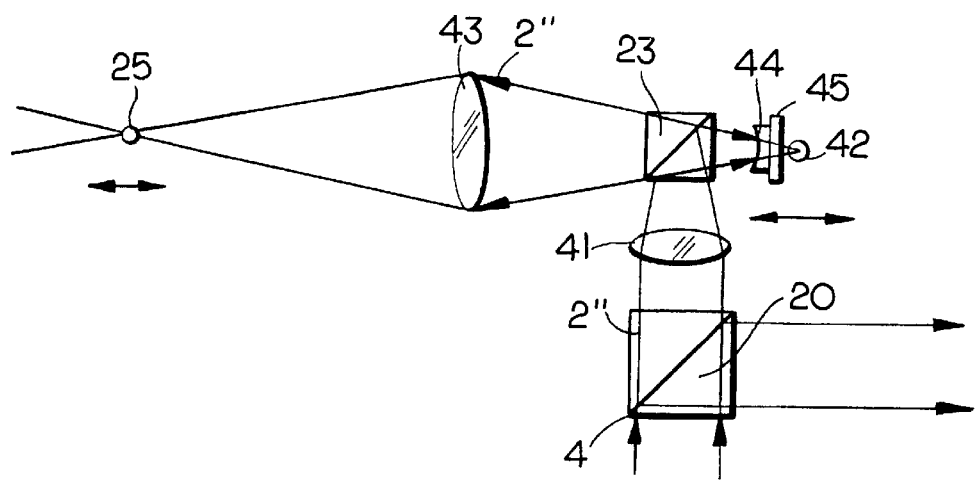
FIG. 10b shows a moving virtual focus produced by means of a moving dispersive lens and a plane mirror moving along with the latter as another alternative for producing a moving focus.

In the arrangement according to FIG. 8a and in the arrangement according to FIG. 8b, a combination of lens and plane mirror, as shown in FIG. 9, or a convex mirror, as shown in FIG. 10a, or some other combination, as shown in FIG. 10b, can also be used as deflecting optics instead of the concave mirror 24.

An essential aspect of the present Application consists in maintaining the adjusted zero path difference (interference condition) between the reference light beam path and measurement light beam path until the dynamic focus (13). For this purpose, the optical imaging of the focus produced by the moving optical element (e.g., the imaging of the focus 22 via optics 21 and the ophthalmic optics in FIG. 6) must be effected in the measurement focus 13 such that the optical path length in the measurement beam remains unchanged until the focus in spite of the focus movement in the measurement object. Considering that in the case of the beam path in FIG. 6 the measurement light traverses the distance between the moving deflecting mirror 24 and the measurement focus 13 two times and the distance between the deflecting mirror 24 and beam splitter an additional two times, it follows that the optical length of this entire path remains constant, also taking into account the moving focus, when the focus 22 is imaged in the fundus oculi in an imaging scale of 1:1. In so doing, the foci 22 and 13 are displaced by 2.$\Delta z$ when the deflecting mirror is displaced by $\Delta z$. The focal length of the optics 21 must equal the focal length of optics 12 in order to ensure the 1:1 imaging. The optics 21 can be designed as zoom optics which are displaceable in the optical axis in order to allow for different eye lengths—and accordingly different focal lengths of their optics. The coherent measurement focus 13 is then displaced by the same distance $\Delta z$ as the measurement mirror and the interference condition is still met for all focus positions. This corresponds to the method according to the invention.

In the arrangement according to FIG. 7, the optical imaging of the focus 25 (via 25') must, on the whole, be effected in the measurement focus 13 in order to maintain the adjusted zero path difference between the measurement light beam path and the reference light beam path (interference condition) such that when the concave mirror 24 is moved by $\Delta z$ the measurement focus 13 is likewise moved by $\Delta z$. This is achieved by means of a total (longitudinal) imaging scale of the focus 25 (it is displaced by 2.$\Delta z$) in the measurement focus 13 of 1:½. Since the depth scale is proportional to the square of the transverse imaging scale according to the known laws of geometrical optics (e.g., H. Haferkorn, *Optik,* J. A. Barth Verlag Leipzig, ISBN 3-335-00363-2, 1994, page 191), the imaging of the focus 25 in the focus 25' must be reduced in the transverse imaging scale of 1:1/$\sqrt{2}$. This can easily be achieved by means of a suitable choice of focal length of the optics 27. In the arrangement shown in FIG. 7, a reduced imaging of the focus 25 is first effected for this purpose by means of optics 27 in the transverse imaging scale 1:1/$\sqrt{2}$ in focus 25' in the focal plane of optics 27', followed by a 1:1 imaging of the focus 25' by means of optics 27' and 12 in the measurement focus 13. The focal length of optics 27' must equal the focal length of optics 12 in order to ensure the 1:1 imaging. In order to allow for different eye lengths—and accordingly different focal lengths of the ophthalmic optics—the optics 27' can be designed as zoom optics. The coherent measurement focus 13 is then displaced by the same distance $\Delta z$ as the measurement mirror and the interference condition is upheld for all focus positions. This corresponds to the method according to the invention.

Obviously, the interference condition can be maintained with a moving coherent measurement focus by a suitable choice of imaging scale of the moving foci (25, 25' and 13) in a number of different ways. For example, in the beam path according to FIG. 7, the focus 22 can be imaged by means of the measurement light mirror 24 in the focus 25 in the (transverse) imaging scale of 1:1/$\sqrt{2}$. In this case, the optics 27 can be omitted and the focus 25 can be imaged in focus 13 in a scale of 1:1, wherein the optics 27' can also be designed as zoom optics in this case in order to allow for different eye lengths. Thus, if the optical path length of the measurement beam path has been made equal to the optical length of the reference light beam path initially via the measurement focus 13, this is upheld along with the interference condition for the coherent measurement focus also when the latter moves through the measurement object. This corresponds to the method according to the invention.

The light returning from the object to be measured is again approximately collimated by the ophthalmic optics (or optics 12) and is focussed in focus 32 by optics 27' and 27 via the beam splitter 26. The focus 32 in the light reflected by the object to be measured likewise makes an axial movement. In this case, with the aid of a pinhole diaphragm 33 which participates in the movement, light components not coming from the coherent measurement focus 13 can be cut out. For this purpose, the pinhole diaphragm 33 must be moved synchronously with the focus 32, which can be achieved, for instance, by means of a scanning table which is controlled by a stepper motor or by means of a piezoelectrically controlled holder or in the some other way.

By means of displacing the deflecting mirror 34 (indicated by a double arrow) for the purpose of adjusting the interference condition, the optical length of the reference light beam path from beam splitter 20, via the deflecting mirror 34, to beam splitter 35 is made equal to the optical length of the measurement beam path, that is, the optical length from the splitter surface 20, via the beam splitter 23, to the concave mirror 24 and from there, via the beam splitter 23, to the focus 25 and continuing via the beam splitter 26 through optics 27, 27' and 12 to the measurement focus 13 of the measurement location and then back, via beam splitter 26, to the focus 32 and continuing to the beam splitter 35 via optics 37. That is, the optical path difference between the reference light beam path and the measurement light beam path remains at zero also for the moving coherent measurement focus 13 and only the light returning from the coherent measurement focus is capable of interference with the reference light. This corresponds to the method according to the invention.

In the interferometer shown in FIG. 7, a convex mirror 40 can also be used as the measurement light mirror as is shown in FIG. 10*a*. For this purpose, the measurement beam 2" is focussed by optics 41 in the center of curvature 42 of the convex mirror 40. The divergent measurement beam 2" returning from this virtual focus (42) is focussed by optics 43 in focus 25. The rest of the beam path can correspond to that shown in FIG. 7. Finally, the convex mirror 40 can also be replaced in a corresponding sense by a combination of a dispersive lens 44 and a plane mirror 45 as is shown in FIG. 10*b*.

Figure 11:
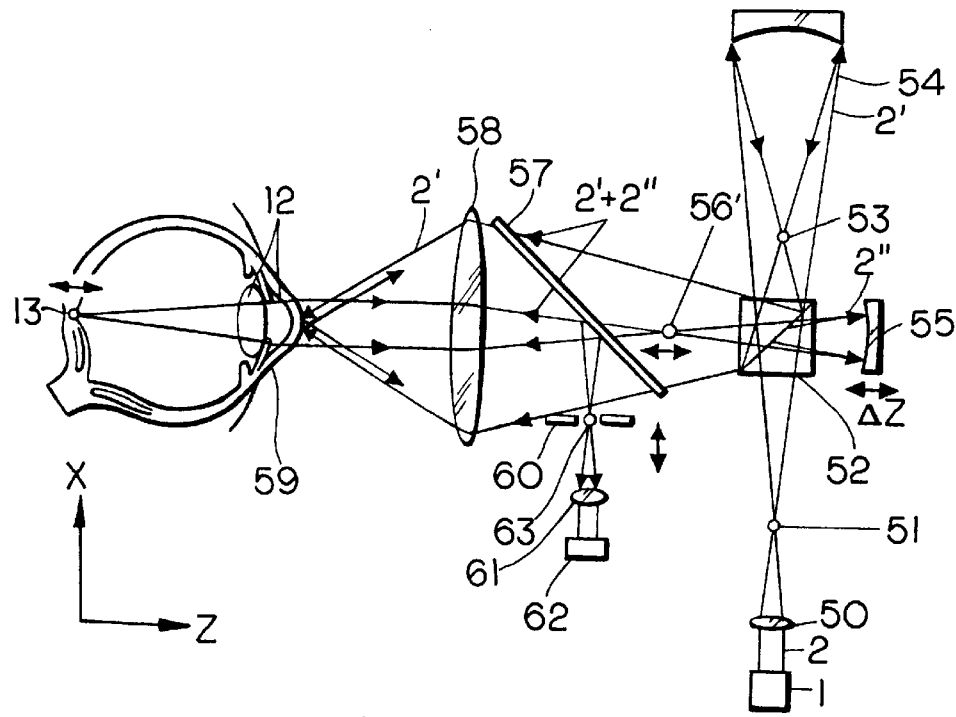
FIG. 11 shows a realization of the method according to the invention using the example of the measurement of intraocular distances by means of the "dual beam" method.

In FIG. 11, the method according to the invention is explained with reference to a beam path in the dual-beam method based on a Michelson interferometer beam path as applied for distance measurement at the retina. In this method, the object to be measured is illuminated by a dual beam 2'+2" comprising the reference beam 2' and the measurement beam 2". These two beams are formed in the following way: The spatially coherent light beam 2 of short coherence length $l_C$ exiting from the light source 1 is focussed in focus 51 by the optics 50. The divergent light bundle traveling from the focus 51 partially passes through the beam splitter 52 and strikes the concave reference mirror 54 as a reference light bundle 2'. The reference light bundle is reflected at the concave reference mirror 54 and is focussed in focus 53. This reference light bundle is directed onto the eye by optics 58 after reflecting at the beam splitter 52. In the dual-beam method, the portion of the light bundle 2' reflected at the front surface of the cornea 59 functions as a reference light at the interferometer output. This light is projected onto the pinhole diaphragm 60 by the optics 58 via the beam splitter 57 and by optics 61 onto the photodetector 62 where it interferes with the measurement light.

Further, the divergent light bundle 2 traveling from the focus 51 is directed to the measurement light mirror (concave mirror) 55 as a measurement light bundle 2" by the beam splitter 52 and, according to the invention, must be focussed by this measurement light mirror 55 in the (transverse) imaging scale of $1:1/\sqrt{2}$ in focus 56'. The concave mirror 55 is moved by distance $\Delta z$ in the z-direction, as is indicated by the double arrow, in order to carry out the measurement in the z-direction by means of a scanning table controlled by a stepper motor, a piezoelectrically controlled holder or in some other way as was already described above. The focus 56' is then also only displaced by $\Delta z$ because of the reduced imaging, and the optical path length in the measurement beam path is reduced at this location by $2.\Delta z$. Further, the focus 56' is imaged on the retina by the optics 58 and ophthalmic optics 12 in the measurement focus 13. If the focal length of the optics 58 is equal to that of the ophthalmic optics 12, this imaging is effected in a scale of 1:1. Accordingly, the measurement focus 13 is displaced by $\Delta z$ and the optical length increases in this portion of the measurement beam path by $2.\Delta z$ (forward and return path). If the optical length of the reference beam path is made equal to the optical length in the measurement beam path to the measurement focus 13 and back to the recombining of the beams in the beam splitter 57 by means of an appropriate position of the deflecting mirror 54, the interference condition for the coherent measurement focus, and accordingly the condition according to the invention, is met in that the optical length in the reference beam path is equal to the optical length in the object beam path as calculated from the beam splitting (52), via the coherent measurement focus (13), to the combination of the beams (57), namely for all positions of the measurement focus. When the coherent measurement focus 13 is displaced in the z-direction, only the light returning from the coherent measurement focus 13 is capable of interference with the reference light and only this light is used for interferometric measurement. This corresponds to the invention.

The light returning from the coherent measurement focus 13 is focussed in focus 63 by the ophthalmic optics 12 and optics 58 via the beam splitter 57. Focus 63 likewise makes an axial movement synchronously with the coherent measurement focus 13. Light components not coming from the coherent measurement focus 13 can be cut out by means of a pinhole diaphragm 60. For this purpose, the pinhole diaphragm 60 must be moved synchronously with the focus 63, which can be achieved, e.g., by means of a scanning table controlled by a stepper motor or by means of a piezoelectrically controlled holder or in some other way.

Figure 12:
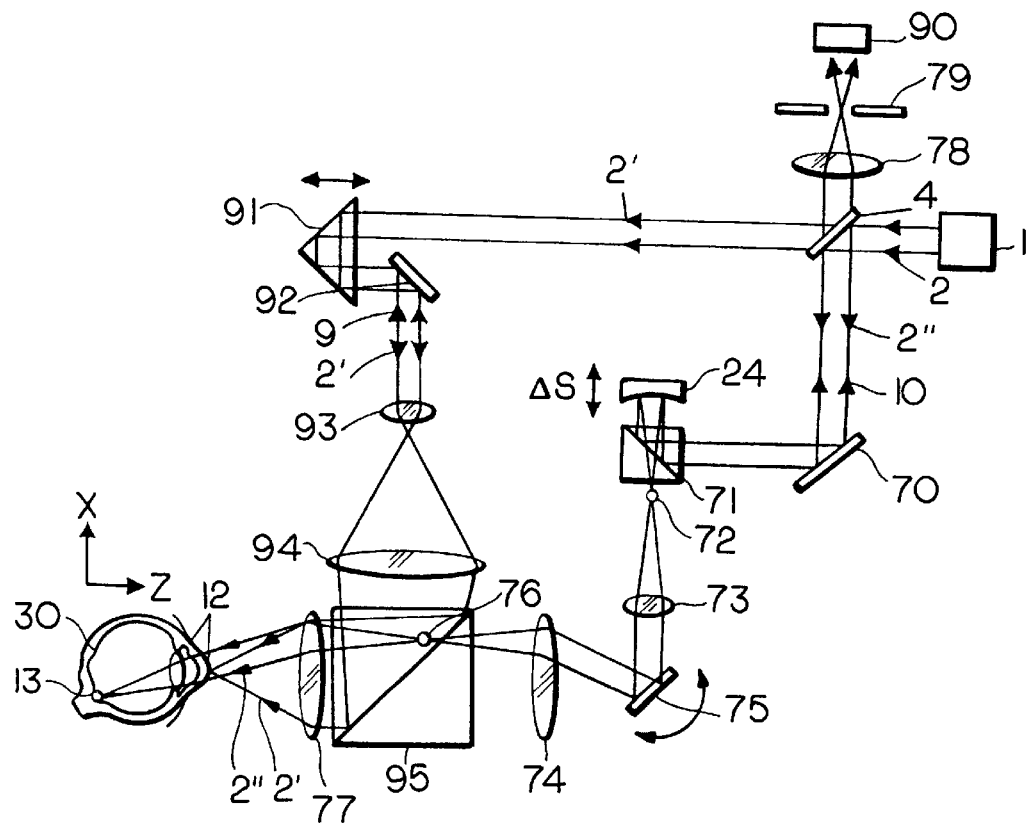
FIG. 12 illustrates the application of the method according to the invention to optical tomography in an example from ophthalmology.

As was already indicated above, a plurality of A-scan measurements closely adjacent to one another in the x-direction is effected in coherence tomography. FIG. 12 shows an example from ophthalmology for obtaining tomograms of the retina based on a modified Mach-Zehnder interferometer. A short-coherence light bundle 2 is emitted by the light source 1. This short-coherence light bundle 2 is divided by the beam splitter surface 4 into a reference beam 2' and a measurement beam 2". The measurement beam 2" is directed to the moving measurement light mirror 24 by the deflecting mirror 70 and beam splitter 71. This measurement light mirror 24 focusses the measurement light bundle 2" in focus 72. Focus 72 is imaged by optics 73 and 74 in focus 76 via the scanning mirror 75 and is further imaged by the optics 77 and the ophthalmic optics 12 in the coherent measurement focus 13. The rotatable mirror 75 directs the measurement light bundle 2" and the focus 13 to different locations at the fundus oculi 30 and thus enables a tomogram to be obtained. The light bundle 10 reflected from the coherent measurement focus 13 takes the same path back to the beam splitter 4, traverses the latter, and is directed to the photodetector 90 by the optics 78 through the pinhole diaphragm 79.

The reference light bundle 2' is directed to the deflecting mirror 92 by the roof prism 91, which serves to balance the optical path lengths in the reference beam path and measurement beam path, and from the deflecting mirror 92 to the optics 93. The reference light bundle 2' is subsequently widened by optics 93 and is focussed and reflected by optics 94 in the vicinity of the cornea via the beam splitter 95. The light bundle 9 reflected by the cornea returns along the same path until the beam splitter 4 where it is directed to the photodetector 90 by the optics 78 through the pinhole diaphragm 79 and interferes with the light bundle coming from the fundus.

The coherence of the focus 13 with the reference light is achieved by means of optical path equilibrium between the reference light bundle and measurement light bundle. In this case, a parallel light bundle strikes the measurement light mirror 24 and is focussed in focus 72. Since the measurement light mirror 24 moves the focus 72 by the same distance in this case, the focus is imaged twice, according to the invention, in a 1:1 imaging: once by optics 73 and 74 after 76 and once by optics 77 and 12 after 13. One of these optical systems can be designed as zoom optics so as to allow for different eye lengths. If the mirror 24 is displaced in the axial direction by distance $\Delta s$, the optical length in the measurement beam path decreases at this location by $2.\Delta s$. Since the focus 13 is displaced by distance $\Delta s$, the optical length of the measurement beam path is reduced at the eye by $2.\Delta s$ (forward and return path) so that the optical length of the measurement beam path as a whole remains equal to the optical length of the reference light beam path. This corresponds to the invention.

It should be mentioned that the application of coherence distance measurement, according to FIGS. 6 and 7, for coherence tomography can also be realized in such a way that a rotating scanning mirror, which directs the measurement beam 2" to different x-positions at the measurement object in which the A-scan measurement is effected, is arranged between the interferometer and the object to be measured (28).

Figure 13:
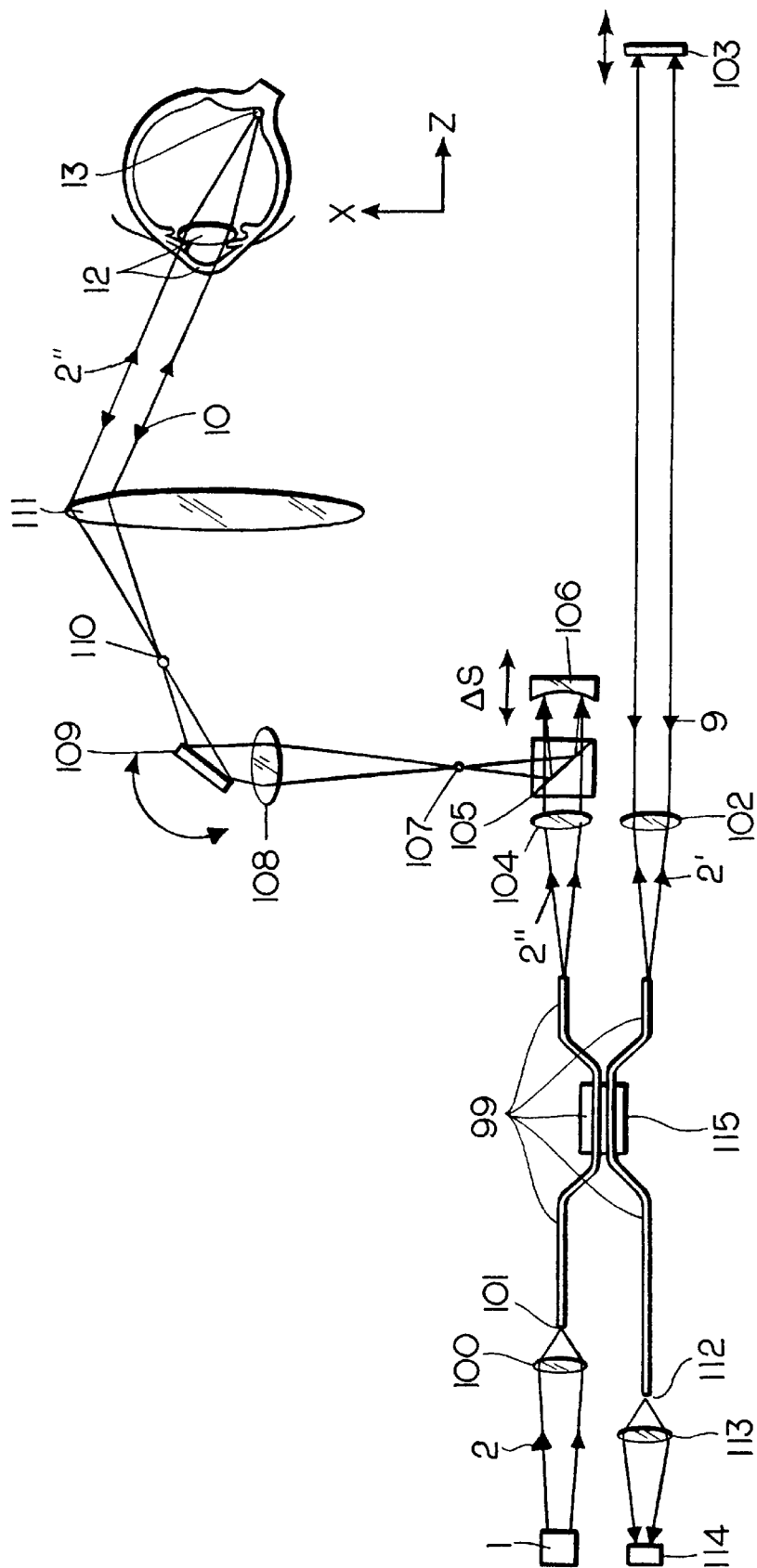
FIG. 13 illustrates the application of the method according to the invention to optical tomography based on a fiber-optics interferometer.

Finally, application of the method according to the invention is illustrated with reference to a fiber-optics tomography device. In FIG. 13, a light source 1 emits a short-coherence light beam 2 which is directed by optics 100 to the input face 101 of a fiber-optics Michelson interferometer 99 with a fiber-optics coupler 115. The light beam 2 is divided into a reference light beam 2' and a measurement light beam 2" by the fiber-optics coupler. The reference light beam 2' is directed by optics 102 to the reference mirror 103 which can be displaced in the beam direction in order to adjust the interference condition (equal optical path length from the beam splitter of the interferometer to the reference mirror 103 and to the coherent measurement focus 13), which is indicated by the double arrow.

The measurement light beam 2" is collimated by optics 104 and is directed through a beam splitter 105 to the measurement light mirror (concave mirror) 106. The concave mirror 106 serves to realize the moving coherent measurement focus. A movement by distance $\Delta s$ is carried out in the beam direction as is indicated by the double arrow. The mirror 106 focusses the measurement bundle 2" in the focus 107 which undergoes a displacement in the direction of the beam axis by the same distance $\Delta s$ as the measurement light mirror 106. Alternatives to the concave mirror 106 can also be used in this case as in FIGS. 8*a*, 8*b*, 9, 10*a* and 10*b*.

The focus 107 is imaged by optics 108 via the scanning mirror 109 in focus 110. The focus 110 is further imaged by optics 111 and ophthalmic optics 12 (cornea and eye lens) in the coherent measurement focus 13 on the fundus oculi. The scanning mirror 109 serves to direct the measurement beam 2" to different positions on the object to be measured (in this case the fundus oculi) in order to realize the tomographic imaging process. The z-positions of the light-reflecting locations in the object to be measured are obtained in this case from the associated positions of the measurement mirror 106.

Since the deflecting mirror 106 generating the focus 107 is illuminated in this case by a parallel light bundle, the focus 107 is displaced by the same distance $\Delta s$ as the deflecting mirror. Therefore, the imaging of the focus 107 must be effected in the measurement focus 13 in the imaging scale of 1:1 as a whole by suitable selection of the focal lengths of the optics 108, 11 and 12 in question. To allow for different eye lengths, the optics 111 can be designed as zoom optics whose focal length would then be approximately identical to the focal length of the eye. The optical length in the measurement beam path then also remains constant with a moving coherent measurement focus 13 and, when suitably adapted, is also equal to the optical length in the reference beam path (interference condition). This corresponds to the invention.

The light bundles 10 and 9 returning from the coherent measurement focus 13 and the reference mirror 103 are superposed in the fiber-optic interferometer, exit at the interferometer output 112 and are directed by optics 113 to the photodetector 114. The electrical photodetector signal U is formed at the photodetector 114 and is used for tomographic image synthesis.

While the foregoing description and drawings represent the preferred embodiments of the present invention, it will be obvious to those skilled in the art that various changes and modifications may be made therein without departing from the true spirit and scope of the present invention.

What is claimed is:

1. In a method for coherence biometry and coherence tomography with increased transverse resolution for measuring the position of light-reflecting locations along a measurement path at the surface of and in the interior of objects by means of a measurement light path of a short-coherence interferometer, in which, for the purpose of achieving interference, the path lengths of the measurement arm and the reference arm are balanced to the same optical length and the positions of the light-reflecting locations in the object along the measurement path are determined from the changes in length of the measurement light path and/or reference light path which are required for these positions to balance the path lengths, wherein the measurement light path is focussed in or on the object to be measured and the measurement focus produced in this way is moved along the measurement path in such a way that it remains coherent with respect to the reference light during the scanning movement, the improvement comprising the step of:

providing the movement of the measurement focus and the wavelength equilibrium required for ensuring its coherence with respect to the reference light by means of the movement of an individual optical component.

2. The method of claim 1, further comprising the step of detecting by a photodetector the measurement light reflected from a measurement focus point on or in the object.

3. In an arrangement for coherence biometry and coherence tomography with increased transverse resolution for measuring the position of light-reflecting locations along a measurement path at the surface of and in the interior of objects by means of a measurement light path of a short-coherence interferometer, in which, for the purpose of achieving interference, the path lengths of the measurement arm and the reference arm are balanced to the same optical length and the positions of the light-reflecting locations in the object along the measurement path are determined from the changes in length of the measurement light path and/or reference light path which are required for these positions to balance the path lengths, wherein the measurement light path is focussed in or on the object to be measured and the measurement focus produced in this way is moved along the measurement path in such a way that it remains coherent with respect to the reference light during the scanning movement, the improvement comprising:

means for providing the movement of the measurement focus and the wavelength equilibrium required for ensuring coherence with respect to the reference light by the movement of an individual optical component.

4. The arrangement for coherence biometry and coherence tomography with increased transverse resolution according to claim 2, wherein a real focus which is produced by a moving concave mirror is imaged in the object to be measured in the measurement light beam of a modified Mach-Zehnder interferometer in a transverse imaging scale of $1:1/\sqrt{2}$.

5. The arrangement for coherence biometry and coherence tomography with increased transverse resolution according to claim 2, wherein a real focus which is produced by a moving concave mirror is imaged in the object to be measured in the measurement light beam of a fiber-optics interferometer in a transverse imaging scale of 1:1.

6. The arrangement for coherence biometry and coherence tomography with increased transverse resolution according to claim 2, wherein a virtual focus which is produced by a moving convex mirror is imaged in the object to be measured in the measurement arm of an interferometer.

7. The arrangement for coherence biometry and coherence tomography with increased transverse resolution according to claim 2, wherein a real or virtual focus produced by moving optics comprising a combination of lens and plane mirror is imaged in the object to be measured in the measurement arm of an interferometer.

8. The arrangement for coherence biometry and coherence tomography with increased transverse resolution according to claim 2, wherein a real focus which is produced by a moving concave mirror is imaged in the object to be measured in the measurement light beam of a Michelson interferometer in a transverse imaging scale of 1:1.

9. The arrangement of claim 3, further comprising a photodetector for detecting measurement light reflected from a measurement focus point on or in the object.

10. In a method for coherence biometry and coherence tomography according to the dual-beam method with increased transverse resolution for measuring the position of light-reflecting locations along a measurement path at the surface of and in the interior of objects based on short-coherence interferometry, in which the object to be measured is illuminated by a dual beam formed of a measurement light beam and a reference light beam exiting from a two-beam interferometer and in which, for the purpose of achieving interference in the light returning from the object to be measured, the path lengths of the measurement arm and the reference arm of said two-beam interferometer are balanced to the same optical length and the positions of the light-reflecting locations in the object along the measurement path are determined from the changes in length in the measurement arm and/or reference arm which are required for these positions for equilibrium, wherein the reference beam is reflected at a stationary light-reflecting location of the object, while the measurement beam is focussed in or on the measurement object, and the measurement focus produced in this way is moved along the measurement path during the measurement, the improvement comprising the step of:

provided the movement of the measurement focus and the interferometric path length equilibrium by means of the movement of an individual optical element.

11. In an arrangement for coherence biometry and coherence tomography according to the dual-beam method with increased transverse resolution for measuring the position of light-reflecting locations along a measurement path at the surface of and in the interior of objects based on short-coherence interferometry, in which the object to be measured is illuminated by a dual beam formed of a measurement light beam and a reference light beam exiting from a two-beam interferometer and in which, for the purpose of achieving interference in the light returning from the object to be measured, the path lengths of the measurement arm and the reference arm of said two-beam interferometer are balanced to the same optical length and the positions of the light-reflecting locations in the object along the measurement path are determined from the changes in length in the measurement arm and/or reference arm which are required for these positions for equilibrium, wherein the reference beam is reflected at a stationary light-reflecting location of the object, while the measurement beam is focussed in or on the measurement object, and the measurement focus produced in this way is moved along the measurement path during the measurement, the improvement comprising:

means for providing the movement of the measurement focus and the interferometric path length equilibrium by the movement of an individual optical element.

12. The arrangement for coherence biometry and coherence tomography with increased transverse resolution according to claim 11, wherein a virtual focus which is produced by a moving convex mirror is imaged in the object to be measured in the measurement arm of an interferometer.

13. The arrangement for coherence biometry and coherence tomography with increased transverse resolution according to claim 11, wherein a real or virtual focus produced by moving optics comprising a combination of lens and plane mirror is imaged in the object to be measured in the measurement arm of an interferometer.

14. The arrangement for coherence biometry and coherence tomography with increased transverse resolution according to claim 11, wherein the dual beam is generated by a modified Michelson interferometer and a real focus which is produced by a moving concave mirror is imaged in the object to be measured in the measurement light beam in the imaging scale of 1:1.

15. The arrangement for coherence biometry and coherence tomography with increased transverse resolution according to claim 11, wherein the dual beam is generated by a modified Mach-Zehnder interferometer and a real focus which is produced by a moving concave mirror is imaged in the object to be measured in the measurement light beam in the transverse imaging scale of $1:1/\sqrt{2}$.

16. An arrangement for scanning an object, comprising:
a light source for emitting light of short coherence length;
means for dividing the light into reference light and measurement light;
optical means for optically focusing the measurement light on or in an object being scanned, a location on or in the object at which the measurement light is focused defining a measurement focus;
means for supplying the reference light onto a detector and for supplying light reflected from the object onto the detector; and
movement means for providing movement of the measurement focus and for providing a wavelength equilibrium between a measurement path and a reference path, said measurement and reference paths representing respective paths on which said measurement and reference light travel, said movement means being carried out by means of movement of an individual optical element.

17. The arrangement of claim 16, wherein said movement means is located within said measurement path.

18. The arrangement of claim 16, further comprising a detector for detecting the combined reference light and light reflected from the object, and wherein the detector is a photodetector.

* * * * *